United States Patent
Anderson et al.

(10) Patent No.: US 8,277,118 B2
(45) Date of Patent: Oct. 2, 2012

(54) DROP COUNTER AND FLOW METER FOR APPARATUS AND METHOD FOR DETERMINING THE THERMAL STABILITY OF FLUIDS

(75) Inventors: David G. Anderson, San Antonio, TX (US); Larry M. Youngblood, Houston, TX (US); Guoxing Yang, Pearland, TX (US); Larry A. Spino, Houston, TX (US); Scott K. Berkhous, Spring, TX (US); Fang Fang, Houston, TX (US)

(73) Assignee: Petroleum Analyzer Company, LP, Houston, TX (US)

( * ) Notice: Subject to any disclaimer, the term of this patent is extended or adjusted under 35 U.S.C. 154(b) by 245 days.

(21) Appl. No.: 12/850,468

(22) Filed: Aug. 4, 2010

(65) Prior Publication Data
US 2012/0014405 A1    Jan. 19, 2012

Related U.S. Application Data

(63) Continuation-in-part of application No. 12/838,104, filed on Jul. 16, 2010.

(51) Int. Cl.
*G01N 33/22* (2006.01)
*G01N 25/00* (2006.01)
*G01F 23/292* (2006.01)

(52) U.S. Cl. .................. 374/43; 73/861.41; 73/290 R (58) Field of Classification Search .............. 374/43, 374/45, 57, 137; 73/61.62, 61.71, 61.72, 73/61.76, 861.41, 290 R, 149; 604/251, 604/253, 255; 250/573, 577, 428; 116/276
See application file for complete search history.

(56) References Cited

U.S. PATENT DOCUMENTS

| | | | | |
|---|---|---|---|---|
| 3,001,397 A | * | 9/1961 | Leonard | 73/861 |
| 3,670,561 A | | 6/1972 | Hundere | |
| 4,432,761 A | * | 2/1984 | Dawe | 604/253 |
| 4,525,163 A | * | 6/1985 | Slavik et al. | 604/65 |
| 4,778,449 A | * | 10/1988 | Weber et al. | 604/65 |
| 5,101,658 A | | 4/1992 | Wilson, III et al. | |
| 5,186,057 A | * | 2/1993 | Everhart | 73/861.41 |
| 5,337,599 A | | 8/1994 | Hundere et al. | |
| 6,562,012 B1 | * | 5/2003 | Brown et al. | 604/253 |
| 6,571,644 B2 | * | 6/2003 | Handschuck | 73/861.41 |
| 7,093,481 B2 | | 8/2006 | Morris | |
| 2003/0171880 A1 | * | 9/2003 | Mitchell et al. | 702/46 |

OTHER PUBLICATIONS

JFTOT 230 Mark III Jet Fuel Thermal Oxidation Tester User's Manual, Alcor, PN: AL-59322, Rev. E, Aug. 14, 2008.

(Continued)

*Primary Examiner* — R. A. Smith
(74) *Attorney, Agent, or Firm* — Gunn, Lee & Cave, P.C.

(57) ABSTRACT

A thermal oxidation tester is shown for determining thermal stability of a fluid, particularly hydrocarbons when subjected to elevated temperatures. The tendency of the heated fluid to oxidize and (1) form deposits on a surface of a heater tube and (2) form solids therein, are both measured at a given flow rate, temperature and time. The measured results are used to determine whether a fluid sample passes or fails the test. Sample flow rate is important in the jet fuel thermal oxidation test. Current practice requires manual drop counting or flow confirmation with the use of volumetric glassware. An apparatus is described to precisely measure the flow rate and automatically perform flow rate check using a drip rate method and/or volumetric method.

17 Claims, 7 Drawing Sheets

OTHER PUBLICATIONS

Maxim, DS2433X Flip Chip Pkg, 1.10 MM Pitch Pkg Code BF623-3, Walker, Jeff, Jul. 16, 2008, Rev. A, effective date Jul. 16, 2008.
JFTOT® 230 Mark III, "Smaller, Simpler, Faster. Improved Controls for Jet Fuel Stability Analysis." PAC, 2 pages.
JFTOT, "Video Tube Deposit Rater", PAC, 2 pages.
ASTM D 3241-09, "Standard Test Method for Thermal Oxidation Stability of Aviation Turbine Fuels (JFTOT Procedure)", ASTM International, 14 pages.

* cited by examiner

DROP COUNTER AND FLOW METER FOR APPARATUS AND METHOD FOR DETERMINING THE THERMAL STABILITY OF FLUIDS

CROSS REFERENCE TO RELATED APPLICATIONS

This is a continuation-in-part of U.S. patent application Ser. No. 12/838,104, filed on Jul. 16, 2010, having at least one overlapping inventor and the same assignee, which application is incorporated herein by reference.

BACKGROUND OF THE INVENTION

1. Technical Field

This invention relates to a drop counter and flow meter for methods and devices measuring the thermal characteristics of fluids. Specifically, this invention relates to automated flow rate check using a drop counter and/or volumetric flow meter incorporated in methods and devices measuring the thermal oxidation tendencies of fuels used in liquid hydrocarbon-burning engines.

2. Background Art

The development of higher performance aviation turbine engines has increased the stress placed on the fuels. In addition to being the fuel source, an aviation turbine fuels may also be used as a heat sink to cool engine components. Combined with an overall decreasing quality of feedstock material for production of fuels, the potential for thermally induced deposition formation is high. Deposits within an aviation turbine engine can (1) reduce heat transfer efficiency, (2) block fuel filters, lines, and nozzles, or (3) result in engine failure.

While various tests were devised and used in the 1950s and 60s to evaluate the thermal oxidation characteristics of jet fuel prior to being used in jet aircraft, Alf Hundere developed the apparatus and method which became the standard in the industry. In 1970, Alf Hundere filed what became U.S. Pat. No. 3,670,561, titled "Apparatus for Determining the Thermal Stability of Fluids". This patent was adopted in 1973 as ASTM D3241 Standard, entitled "Standard Test Method for Thermal Oxidation Stability of Aviation Turbine Fuels", also known as the "JFTOT® Procedure". This early Hundere patent was designed to test the deposition characteristics of jet fuel by determining (1) deposits on the surface of a heater tube at an elevated temperature and (2) differential pressure across a filter due to collection of particulate matter. To this day, according to ASTM D3241, the two critical measurements are still (1) the deposits collected on a heater tube and (2) differential pressure across the filter due to the collection of particulate matter on the filter.

According to ASTM D3241, 450 mL of fuel flows across an aluminum heater tube at a specified rate during a 2.5-hour test period at an elevated temperature. Currently six different models of JFTOT®[1] instruments are approved for use in the ASTM D3241-09 Standard. The "09" refers to the current revision of the ASTM D3241 Standard.

[1] JFTOT® is the registered trademark of Petroleum Analyzer Company, LP.

While over the years various improvements have been made in the apparatus to run the tests, the basic test remains the same. Improvements in the apparatus can be seen in U.S. Pat. Nos. 5,337,599 and 5,101,658. The current model being sold is the JFTOT® 230 Mark III, which is described in further detail in the "Jet Fuel Thermal Oxidation Tester—User's Manual". The determination of the deposits that occur on the heater tube can be made visually by comparing to known color standards or can be made using a "Video Tube Deposit Rater" sold under the Alcor mark.

The determination of the amount of deposits formed on the heater tube at an elevated temperature is an important part of the test. The current ASTM D3241 test method requires a visual comparison between the heater tube deposits and known color standard. However, this involves a subjective evaluation with the human eye. To take away the subjectivity of a person, an electronic video tube deposit rater was developed.

When performing a test under ASTM D3241 Standard, it is important to accurately measure the rate of flow of the test sample. However, this is difficult to perform manually due to slow rate of flow which is in drops per minute.

Once the thermal oxidation stability test has been performed on a batch of fuel, the recorded information and the heater tube are preserved to show the batch of fuel was properly tested. The information that was recorded when testing a batch of fuel is maintained separately from the heater tube itself. This can cause a problem if one or the other is misplaced or lost. Inaccurate information and/or conclusions occur if the wrong set of data is associated with the wrong heater tube.

BRIEF SUMMARY OF THE INVENTION

It is an object of the present invention to provide an apparatus and method for testing thermal oxidation stability of fluids, particularly aviation fuels with an improved drop counter and flow meter.

It is another object of the present invention to provide an apparatus and method to measure the tendency of fuels to form deposits when in contact with heated surfaces, the apparatus including an improved drop counter and flow meter.

It is another objective of the present invention to provide a drop counter and flow meter for an apparatus and method for testing the thermal oxidation tendency of fuels utilizing a test sample to determine if solid particles will form in the fuel at an elevated temperature and pressure.

It is another objective of the present invention to provide a drop counter and flow meter for an apparatus and method for determining thermal oxidation stability of a batch of fuel by testing a sample at an elevated temperature and pressure to determine (1) deposits that form on a metal surface and (2) solid particles that form in the fuel.

It is another objective of the present invention to provide an improved drop counter and flow meter to accurately measure the flow rate of the fuel being tested.

It is yet another objective of the present invention to provide a drop counter and flow meter to accurately measure the flow rate of the fuel being tested for thermal oxidation stability.

A drop counter and flow meter is provided when testing a fuel for thermal oxidation stability, in which the drop counter and flow meter automatically counts drops and accurately measures the flow rate during testing. The flow rate is controlled by an embedded computer through a sample drive pump during test, and then verified by the drop counter and flow meter. An infrared LED and photodiode pair is used to count the number of drops of fuel and also monitor the fuel level inside of a container. The time to fill a given volume from one level to a second level can be used to determine flow rate.

DESCRIPTION OF THE PREFERRED EMBODIMENT

Figure 1:
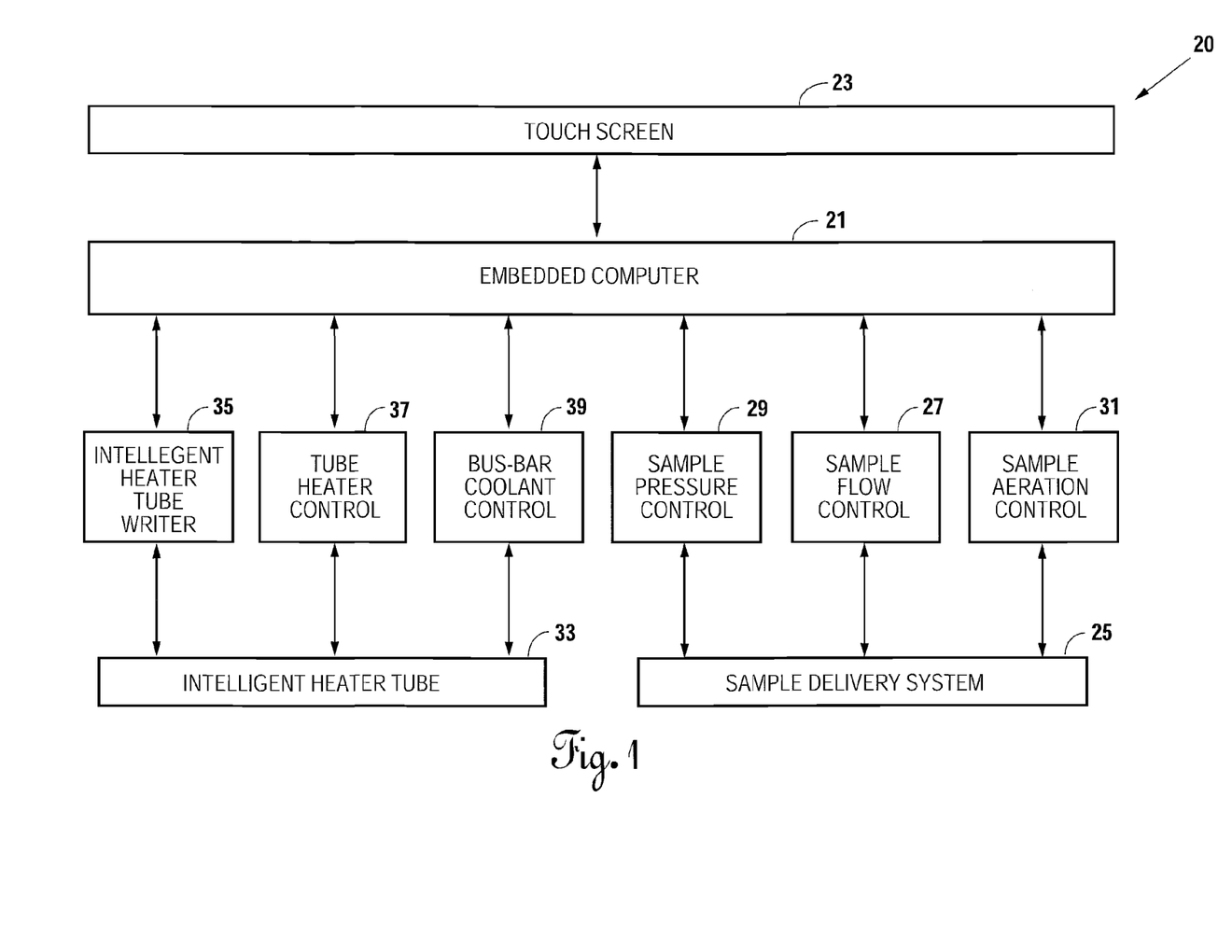
FIG. 1 is a general block diagram of a thermal oxidation stability test apparatus illustrating flow and electrical controls.

FIG. 1 is a schematic block diagram of a thermal oxidation stability tester referred to generally by the reference numeral 20. The thermal oxidation stability tester 20 has an embedded computer 21 with a touch screen 23 for user interface. While many different types of programs could be run, in the preferred embodiment, Applicant is running C++ in the embedded computer 21. The touch screen 23 displays all of the information from the thermal oxidation stability tester 20 that needs to be conveyed to the user. The user communicates back and forth with the embedded computer 21 through the touch screen 23. If a batch of fuel is to be tested, a test sample is put in the sample delivery system 25.

It is required by the test to ensure the test sample is oxygen saturated through aeration. Therefore, the embedded computer 21 operates a sample aeration control 31 for a period of time to make sure the sample is fully aerated. The aeration of the sample takes place at the beginning of the test.

The embedded computer 21 turns on a sample flow control 27, which is a pump used to deliver the sample throughout the thermal oxidation stability tester 20. Simultaneous with the sample flow control 27 pumping the test sample throughout the system, sample pressure control 29 maintains a fixed pressure throughout the system. It is important to maintain pressure in the system to prevent boiling of the test sample when at elevated temperatures. In the present thermal oxidation stability tester 20, the sample is maintained at approximately 500 psi during the thermal oxidation stability test.

Also, the embedded computer 21 controls parameters affecting the intelligent heater tube 33 via intelligent heater tube 33. The test data is recorded to the heater tube writer 35 from the embedded computer 21. Critical test parameters are recorded on a memory device on an end of the intelligent heater tube via the intelligent heater tube writer 35. The rating of the deposit formed on the intelligent heater tube 33 will be recorded on the memory device at a later time.

In performing the thermal oxidation stability test on a test sample, the intelligent heater tube 33 is heated by tube heater control 37. The tube heater control 37 causes current to flow through the intelligent heater tube 33, which causes it to heat up to the temperature setpoint.

To prevent the hot intelligent heater tube 33 from heating other parts of the thermal oxidation stability tester 20, bus-bar coolant control 39 provides coolant to upper and lower bus-bars holding each end of the intelligent heater tube 33. This results in the center section of the intelligent heater tube 33 reaching the prescribed temperature while the ends of the intelligent heater tube 33 are maintained at a lower temperature. This is accomplished by flowing coolant via the bus-bar coolant control 39 across the ends of the intelligent heater tube 33.

The test parameters, such as the dimension of the heater tube, pressure of the test sample or flow rate are fixed by ASTM D3241. However, the control of the equipment meeting these parameters are the focus of this invention.

Figure 2:
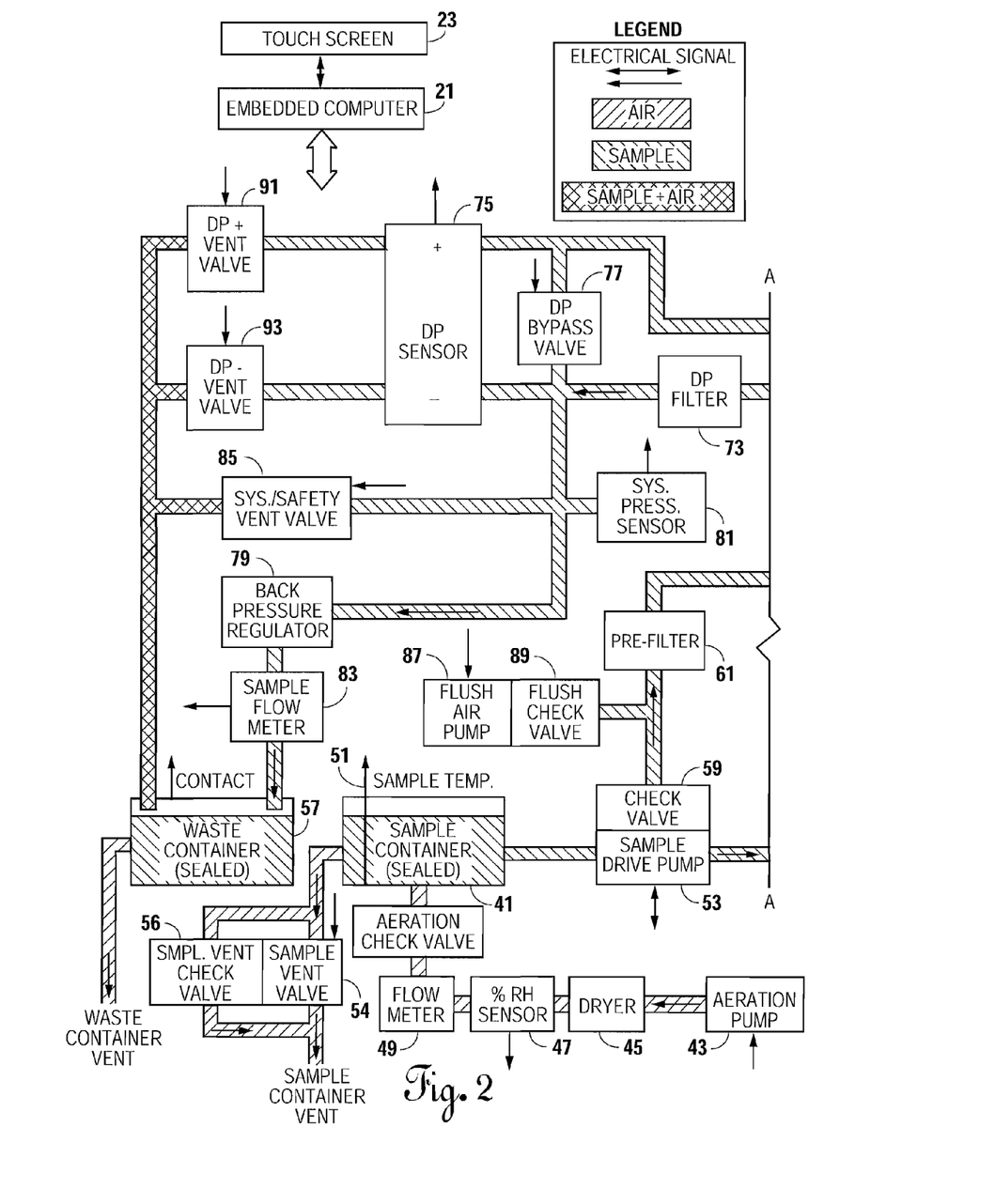
FIGS. 2 and 2A are a more detailed block diagram showing a thermal oxidation test apparatus used to perform ASTM D3241 Standard.
Figure 2A:
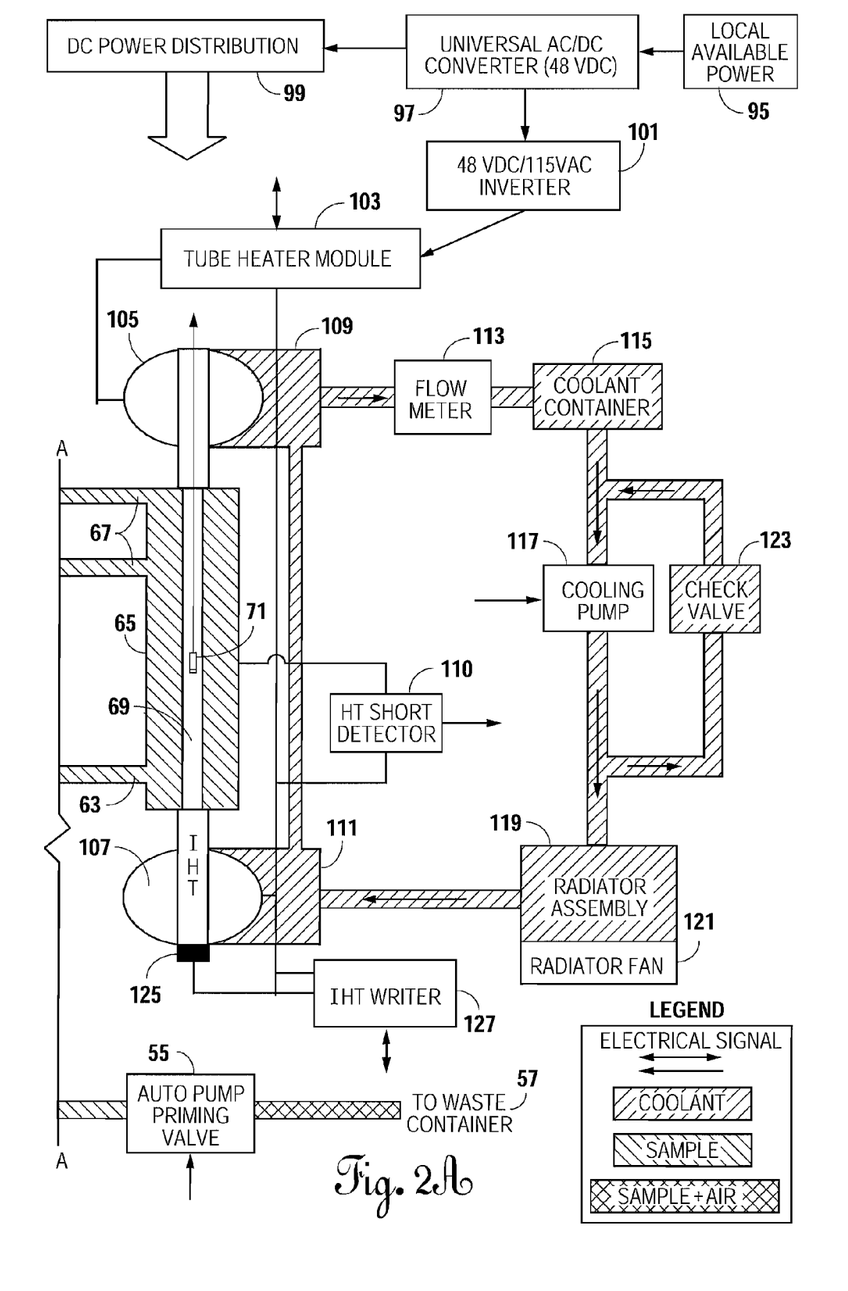

Referring now to FIGS. 2 and 2A in combination, a schematic flow diagram is shown connecting the mechanical and electrical functions. The embedded computer 21 and the touch screen 23 provide electrical signals as indicated by the arrows. A test sample is contained in the sample container 41. To make sure the sample in the sample container 41 is fully aerated, an aeration pump 43 is turned ON. The aeration pump 43 pumps air through a dryer 45 where the air is dehumidified to remove moisture. From the dryer 45, a percent relative humidify sensor 47 determines the humidity level of the pumped air and provides that information to the embedded computer 21. Assuming the percent humidity of the pumped air is sufficiently low, the test procedure will continue pumping air through the flow meter 49 and aeration check valve 50 into the sample container 41. During aeration, flow meter 49 should record approximately 1.5 liters of air per minute. Since the flow meter 49 runs for approximately six minutes, the aeration pump 43 will sparge approximately nine liters of air into the test sample. This is sufficient time to saturate the test sample with dry air.

Within the sample container 41, a sample temperature measurement 51 is taken and provided to the embedded computer 21. The sample temperature measurement 51 is to ensure that the test sample is between 15°-32° C. If the test sample is outside of this temperature range, results can be impacted. Therefore, if the test sample is outside this temperature range, the embedded computer 21 would not let the test start.

Once the test sample has been aerated and if all the other parameters are within tolerance, then the sample drive pump 53 will turn ON. The sample drive pump 53 is a single piston HPLC pump, also known as a metering pump. With every stroke of the piston, a fixed volume of the sample is delivered. The speed of the sample drive pump 53 is controlled so that it pumps 3 mL/min of the test sample. The sample drive pump 53 is configured for fast refill which minimizes the need for manual pump priming. Pulsations, associated with pumps of this design are minimized with the use of a pulse dampener and a coil tubing on the outlet side as will be subsequently described.

To get air out of the tubing between the sample container 41 and the sample drive pump 53 at the start of the test, an auto pump priming valve 55 is opened, a sample vent valve 54 is closed and the aeration pump 43 is turned ON by the embedded computer 21. The auto pump priming valve 55 opens and remains open while a combination of sample and air is discharged into waste container 57. At the same time, the aeration pump 43 provides positive pressure in the sample container 41 to force test sample from the sample container 41 to the sample drive pump 53. The sample vent valve 54 closes to prevent venting of the air pressure to atmosphere to maintain a pressure of 2 to 3 psi. A sample vent check valve 56 across the sample vent valve 54 opens at 5 psi to prevent the pressure in the sample container 41 from exceeding 5 psi. Once the sample drive pump 53 starts pumping the test sample, auto pump priming valve 55 will close and the sample vent valve 54 will open. Thereafter, the sample drive pump 53 will pump the test sample through check valve 59 to the prefilter 61. The check valve 59 prevents fluid from flowing backwards through the sample drive pump 53. The check valve 59 operates at a pressure of approximately 5 psi. The check valve 59 prevents siphoning when the sample drive pump 53 is not pumping. Also, check valve 59 prevents fluid from being pushed backwards into the sample drive pump 53.

The prefilter 61 removes solid particles in the test sample that could affect the test. The prefilter 61 is a very fine filter, normally in the order of 0.45 micron in size. The purpose of the prefilter 61 is to make sure particles do not get into the test filter as will be described. The prefilter 61 is replaced before every test From the prefilter 61, the test sample flows through an inlet 63 into the cylindrical heater tube test section 65. Outlet 67, while illustrated as two separate outlets, is actually a single outlet at the upper end of the cylindrical heater tube test section 65. Extending through the cylindrical heater tube test section 65 is the intelligent heater tube 69, sealed at each end with ceramic bushings and an o-ring (not shown). While the test sample flows through the cylindrical heater tube test section 65 via inlet 63 and outlet 67 and around the intelligent heater tube 69, the housing of the cylindrical heater tube test section 65 is electrically isolated from the intelligent heater tube 69. Only the test sample comes in contact with the center section of the intelligent heater tuber 69. Inside of the intelligent heater tube 69 is a thermocouple 71 that sends a signal back to the embedded computer 21 as to the temperature of the center section of the intelligent heater tube 69.

Test sample flowing from the cylindrical heater tube test section 65 flows through a differential pressure filter 73, commonly called the "test filter". In a manner as will be explained in more detail, the intelligent heater tube 69 heats up the test sample inside of the cylindrical heater tube test section 65 to the test parameter set point. Heating of the test sample may result in degradation of the test sample, or cause solid particles to form. The solid particles may deposit on the center section of the intelligent heater tube 69, and/or may collect on the differential pressure filter 73. The pressure drop across the differential pressure filter 73 is measured by differential pressure sensor 75. Pressure across the differential pressure filter 73 is continuously monitored by the embedded computer 21 through the differential pressure sensor 75. When the pressure across the differential pressure filter 73 exceeds a predefined differential of approximately 250 mm to 280 mm of mercury, the differential pressure bypass valve 77 opens to relieve the pressure. By test definition, exceeding a differential pressure of 25 mm Hg results in failure of the test.

For this test to be performed, the test sample must remain as liquid. At typical testing temperatures of 250° C. to 350° C., many hydrocarbon fuels will transition to the vapor phase at ambient pressures. To keep the test sample in the liquid phase, the back pressure regulator 79 maintains approximately 500 psi pressure in the system. This system pressure is monitored by the system pressure sensor 81, which reports information to the embedded computer 21. During a test, normal flow of a test sample is through differential pressure filter 73 and through the back pressure regulator 79. From the back pressure regulator 79, the test sample flows through sample drop counter and flow meter 83 to waste container 57. The sample drop counter and flow meter 83 automatically counts drops and accurately measures the flow rate of the test sample during the test. The sample drop counter and flow meter 83 provides sample drop counts and flow rate information to the embedded computer 21.

A system/safety vent valve 85 is connected into the system and controlled via the embedded computer 21. The system/safety vent valve 85 acts to relieve excess system pressure in the case of power loss, improperly functioning system components or other system failures. In the event of this occurrence, the system pressure sensor 81 sends a signal to the embedded computer 21, triggering the system/safety vent valve 85 to open and relieve excess pressure. Also, at the completion of a test, the system/safety vent valve 85 opens to vent pressure from the system. The system/safety vent valve 85 is normally set to the open position requiring a program command from the embedded computer 21 to close the system/safety vent valve 85. Therefore, if power is lost, the system/safety vent valve 85 automatically opens.

At the end of the test, after the system/safety vent valve 85 is opened and system pressure is relieved, the flush air pump 87 turns ON and flushes air through flush check valve 89 to remove the test sample from the system. The flush air pump 87 pushes most of the test sample out of the system via the system/safety vent valve 85 into the waste container 57.

The system may not operate properly if there are air pockets or air bubbles in the system. During a test, it is important to maintain an air-free system. Therefore, at the beginning of each test, the solenoid operated differential pressure plus vent valve 91 and the differential pressure minus vent valve 93 are opened, flushed with test sample, and vented to remove any air pockets that may be present. During the beginning of each test, the position of the differential pressure vent valves 91 and 93 ensure there is no air in the differential pressure lines.

If the waste container 57 is properly installed in position, a signal will be fed back to the embedded computer 21 indicating the waste container 57 is correctly connected. This also applies for the sample container 41 which sends a signal to the embedded computer 21 when it is properly connected. The system will not operate unless both the waste container 57 and the sample container 41 are properly positioned.

The center portion of the intelligent heater tube 69 is heated to the test parameter set point by flowing current through the intelligent heater tube 69. Instrument power supplied for current generation and all other instrument controls is provided through local available power 95. Depending on local power availability, local available power 95 may vary drastically. In some areas it is 50 cycles/sec. and in other areas it is 60 cycles/sec. The voltage range may vary from a high of 240 Volts down to 80 Volts or less. A universal AC/DC converter 97 takes the local available power 95 and converts it to 48 Volts DC. With the universal AC/DC converter 97, a good, reliable, constant 48 Volts DC is generated.

The 48 Volts DC from the universal AC/DC converter 97 is distributed throughout the system to components that need power through the DC power distribution 99. If some of the components need a voltage level other than 48 Volts DC, the DC power distribution 99 will change the 48 Volts DC to the required voltage level.

To heat the intelligent heater tube 69, the 48 Volts from the universal AC/DC converter 97 is converted to 115 Volts AC through 48 Volt DC/115 Volts AC inverter 101. While taking any local available power 95, running it through a universal AC/DC converter 97 and then changing the power back to 115 Volts AC through a 48 Volts DC/115 Volts AC inverter 101, a stable power supply is created. From the 48 Volts DC/115 Volts AC inverter 101, power is supplied to the heater tube module 103. The heater tube module 103 then supplies current that flows through the intelligent heater tube 69 via upper clamp 105 and lower clamp 107. The heater tube module 103 is controlled by the embedded computer 21 so that during a normal test, the thermocouple 71 inside of the intelligent heater tube 69 will indicate when the intelligent heater tube 69 has reached the desired temperature.

While the center section of the intelligent heater tube 69 heats to desired test set point, the ends of the intelligent heater tube 69 should be maintained near room temperature. To maintain the ends of the intelligent heater tube 69 near room temperature, a coolant flows through an upper bus-bar 109 and lower bus-bar 111. The coolant inside the upper bus-bar 109 and lower bus-bar 111 cools the upper clamp 105 and lower clamp 107 which are attached to the ends of the intelligent heater tube 69. The preferred cooling solution is a mixture of approximately 50% water and 50% antifreeze (ethylene glycol). As the coolant flows to the coolant container 115, the flow is measured by flow meter 113. To circulate the coolant, a cooling pump 117 pumps the coolant solution into a radiator assembly 119. Inside of the radiator assembly 119, the coolant is maintained at room temperature. The radiator fan 121 helps remove heat from the coolant by drawing air through the radiator assembly 119. From the radiator assembly 119, the coolant flows into the lower bus-bar 111 then through upper bus-bar 109 prior to returning via the flow meter 113.

The flow meter 113 is adjustable so that it can ensure a flow of approximately 10 gal./hr. The check valve 123 helps ensure the cooling system will not be over pressurized. Check valve 123 will open at around 7 psi, but normally 3-4 psi will be developed when running the coolant through the entire system.

To determine if the intelligent heater tube 69 is shorted out to the housing (not shown in FIGS. 2 and 2A), a heater tube short detector 110 monitors a short condition. If a short is detected, the embedded computer 21 is notified and the test is stopped.

On one end of the intelligent heater tube 69 there is a memory device 125 to which information concerning the test can be recorded by IHT writer 127. While a test is being run on a test sample, the IHT writer 127 will record information into the memory device 125. At the end of the test, all electronic information will be recorded onto the memory device 125 of the intelligent heater tube 69, except for the manual tube deposit rating. To record this information, the intelligent heater tube 69 will have to be moved to another location to record the deposit rating either (a) visually or (b) through a Video Tube Deposit Rater. At that time, a second IHT writer will write onto the memory device 125. The Video Tube Deposit Rater may be built into the system or may be a standalone unit.

The intelligent heater tube 69 is approximately 6-3/4" long. The ends are approximately 3/16" in diameter, but the center portion that is heated is approximately 1/8" in diameter. Due to very low electrical resistance of aluminum, approximately 200 to 250 amps of current flows through the intelligent heater tube 69. Both the voltage and the current through the intelligent heater tube 69 is monitored by the embedded computer 21, but also the temperature of the center section of the intelligent heater tube 69 is monitored by the thermocouple 71 which is also connected to the embedded computer 21. The objective is to have the center section of the intelligent heater tube 69 at the required temperature. To generate that type of stable temperature, a stable source of power is provided through the universal AC/DC converter 97 and then the 48 VDC/115 VAC inverter 101. By using such a stable source of power, the temperature on the center section of the intelligent heater tube 69 can be controlled within a couple of degrees of the required temperature.

Figure 3:
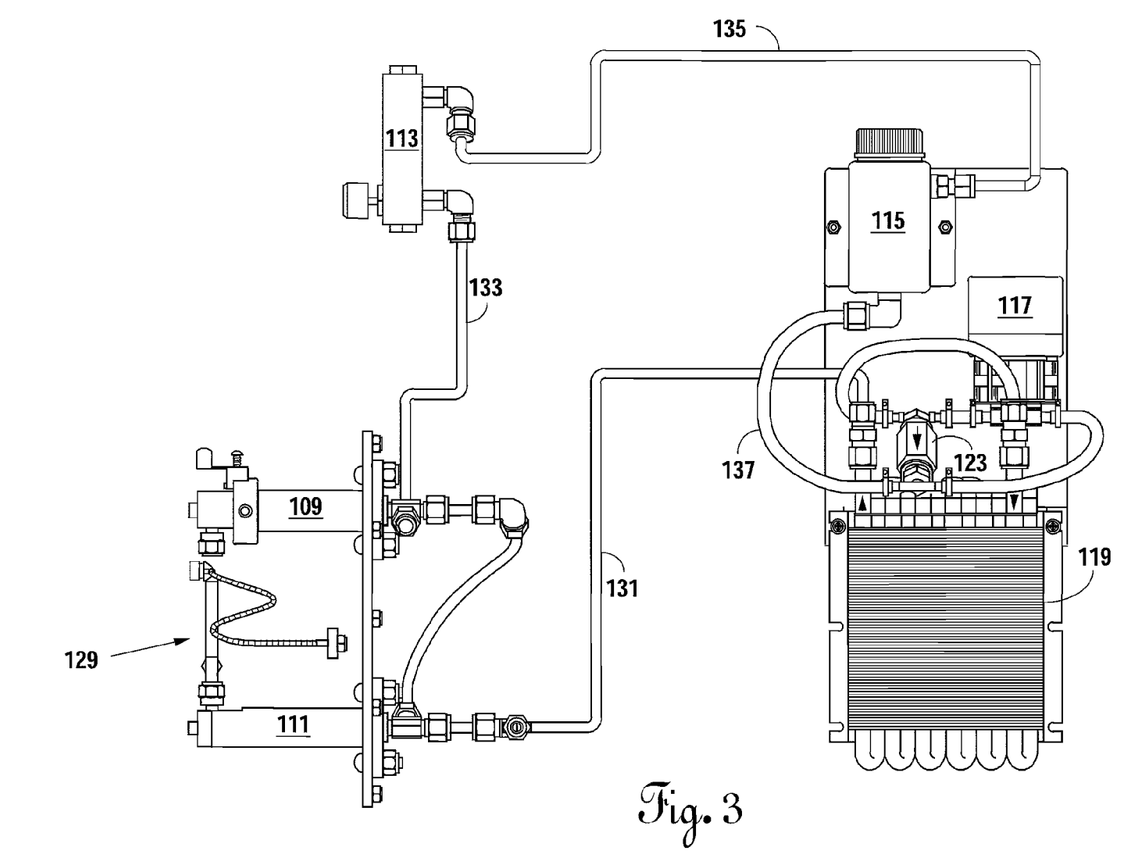
FIG. 3 is a pictorial diagram of the coolant flow for FIGS. 2 and 2A.

Referring now to FIG. 3 of the drawings, a pictorial representation of the coolant flow during a test is illustrated. Like numbers will be used to designate similar components as previously described. A pictorial illustration of the heater tube test section 129 is illustrated on the lower left portion of FIG. 3. Coolant from the radiator assembly 119 is provided to the lower bus-bar 111 and upper bus-bar 109 via conduit 131. From the upper bus-bar 109, the coolant flows via conduit 133 to flow meter 113. From flow meter 113, the coolant flows through conduit 135 to the coolant container 115. The cooling pump 117 receives the coolant through conduit 137 from the coolant container 115 and pumps the coolant into radiator assembly 119. If the pressure from the cooling pump 117 is too high, check valve 123 will allow some of the coolant to recirculate around the cooling pump 117. FIG. 3 is intended to be a pictorial representation illustrating how the coolant flows during a test.

Figure 4:
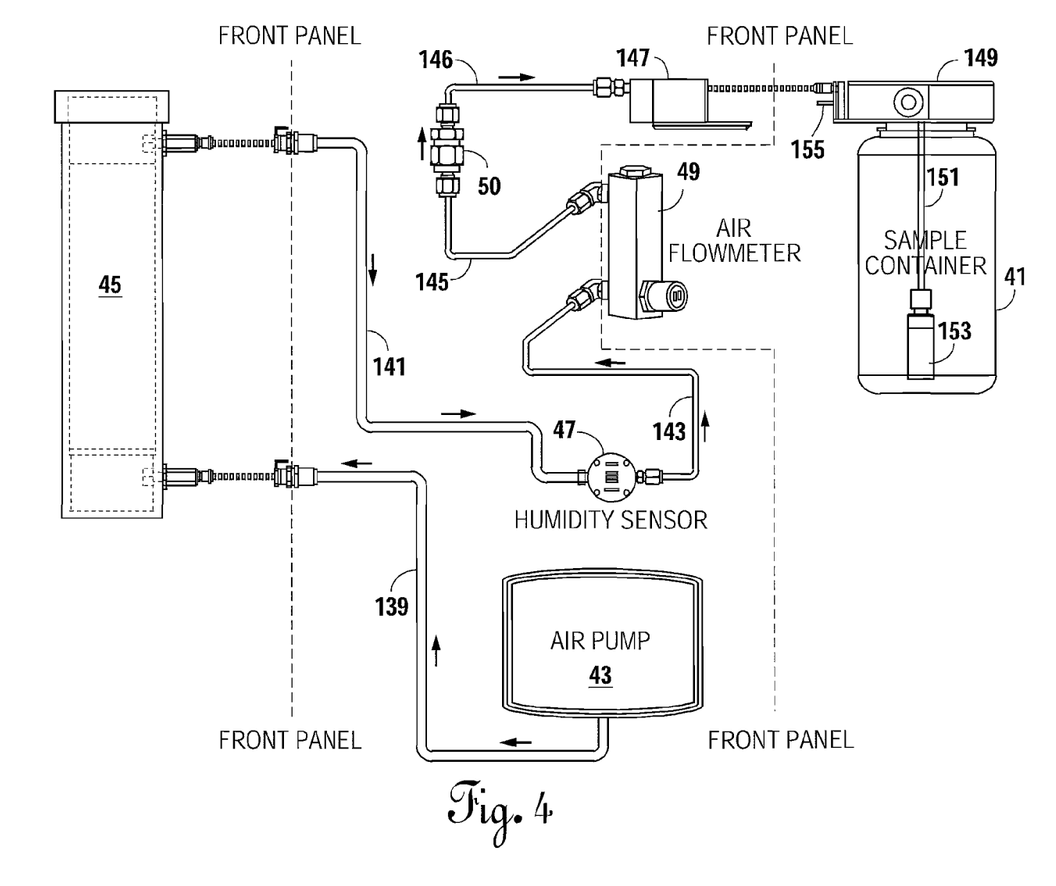
FIG. 4 is a pictorial diagram of the airflow in FIGS. 2 and 2A

Likewise, FIG. 4 is a pictorial representation of the aeration system for the test sample. Similar numbers will be used to designate like components as previously described. An aeration pump 43 pumps air through conduit 139 to a dryer 45. The dryer 45 removes moisture from the air to prevent the moisture from contaminating the test sample during aeration. From the dryer 45, the dried air will flow through conduit 141 to humidity sensor 47. If the percent relative humidity of the dried air blowing through conduit 141 exceeds a predetermined amount of 20% relative humidity, the system will shut down. While different types of dryers 45 can be used, it was found that Dry-Rite silica gel desiccant is an effective material for producing the desired relative humidity.

From the percent humidity sensor 47, the dried air flows through conduit 143 to flow meter 49, which measures the air flow through conduit 143 and air supply conduit 145. From air supply conduit 145, the dried air flows through aeration check valve 50 and conduit 146 sample container arm mounting clamp 147 and sample container arm 149 to aeration conduit 151 located inside of sample container 41. In the bottom of sample container 141, a glass frit 153 connects to aeration conduit 151 to cause the dried air to sparge through the test sample in sample container 41. When the sample container 41 is in place and the sample container arm 149 is connected to the sample container arm mounted clamp 47, contact 155 sends a signal to the embedded computer 21 (see FIG. 2) indicating the sample container 41 is properly installed.

Figure 5:
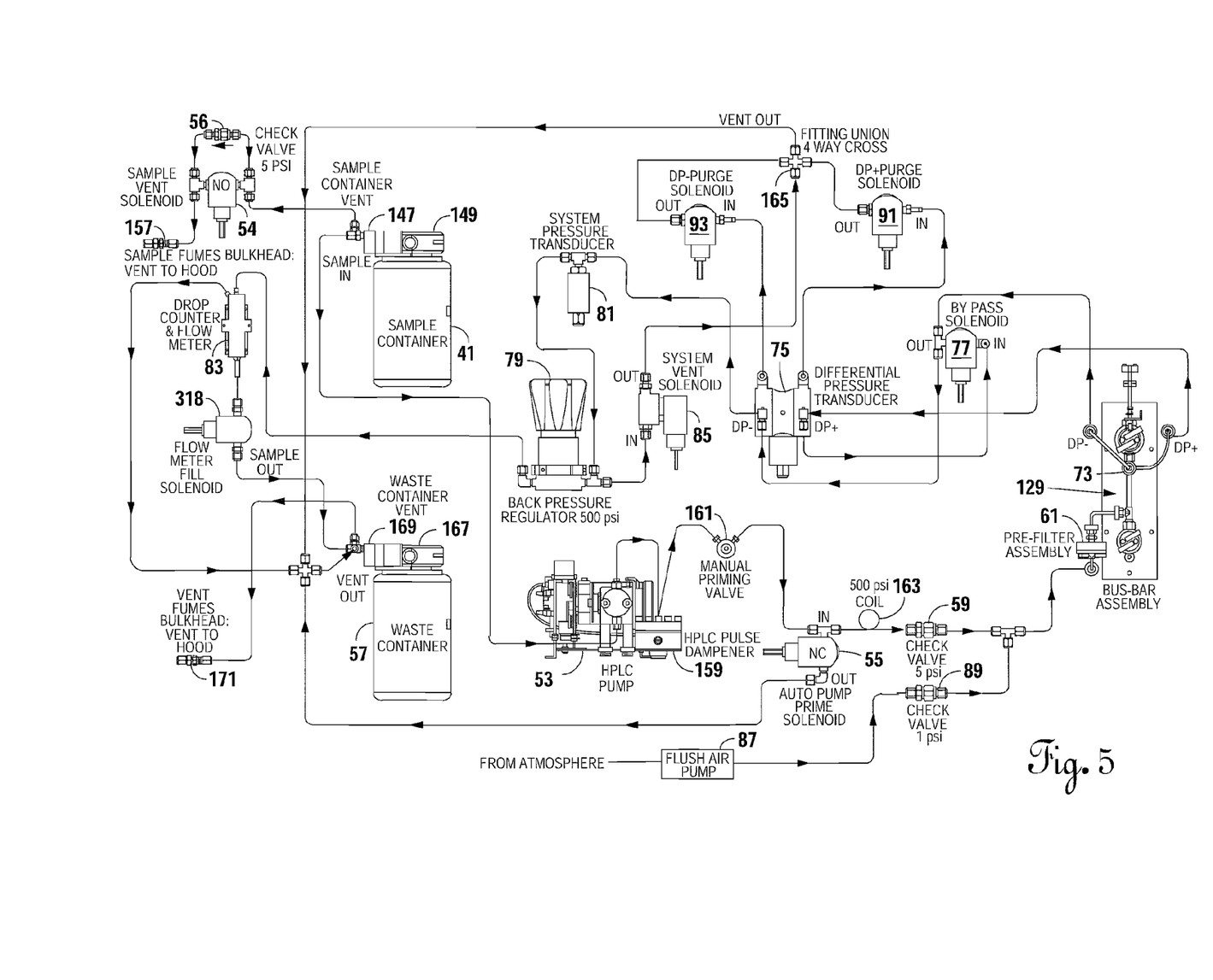
FIG. 5 is a pictorial diagram showing flow of the test sample in FIGS. 2 and 2A.

Referring now to FIG. 5, a pictorial illustration of the flow of the test sample in connection with FIGS. 2 and 2A is shown in a schematic flow diagram. The test sample is contained in sample container 41, which is connected via sample container arm 149 to the sample container arm mounting clamp 147. Vapors given off by the test sample are discharged through a vent 157, normally through a vent hood to atmosphere. Simultaneously, the sample drive pump 53 draws some of the test sample out of the sample container 41. The sample drive pump 53 is a single stroke HPLC pump connected to a pulse dampener 159. While the pulse dampener 159 may be configured a number of ways, the pulse dampener 159 in the preferred configuration has a diaphragm with a semi-compressible fluid on one side of the diaphragm. This fluid is more compressible than the test sample thereby reducing pressure changes on the test sample flow discharged from the sample drive pump 53. The sample drive pump 53 is connected to auto pump priming valve 55. During start-up, the closed auto pump priming valve 55 opens until all of the air contained in the pump and the lines are discharged into the waste container 57. In case it is needed, a manual priming valve 161 is also provided. Additionally, the aeration pump 43 (see FIG. 2) is turned ON to provide a slight pressure in the sample container 41 of about 2 to 3 psi. The sample vent valve 54 closes to prevent this pressure from escaping to atmosphere. This pressure will help push the fluid sample from the sample container 41 to the inlet of the sample drive pump 53. The 5 psi check valve 56 prevents the pressure in the sample container exceeding 5 psi. During the test, coil 163 also provides further dampening in addition to the pulse dampener 159. Check valve 59 ensures there is no back flow of the sample fuel to the sample drive pump 53. However, at the end of a test, flush check valve 89 receives air from flush air pump 87 to flush the test sample out of the system.

During normal operation of a test, the sample fuel will flow through check valve 59 and through a prefilter 61 removing most solid particles. Following the prefilter 61, the test sample flows into the heater tube test section 129 and then through the differential pressure filter 73. Each side of the differential pressure filter 73 connects to the differential pressure sensor 75. Also connected to the differential pressure filter 73 is the back pressure regulator 79. The pressure on the system is continuously monitored through the system pressure transducer 81. If for any reason pressure on the system needs to be released, system/safety vent valve 85 is energized and the pressurized test sample is vented through the four-way cross connection 165 to the waste container 57.

At the beginning of the test, to ensure there is no air contained in the system, the differential pressure plus vent valve 91 and the differential pressure minus vent valve 93 are opened to vent any pressurized fluid through the four-way cross connection 165 to the waste container 57.

In case the differential pressure filter 73 clogs so that the differential pressure exceeds a predetermined value, differential pressure bypass valve 77 will open to relieve the pressure.

To determine the exact flow rate of the test sample through the system, the sample flow meter 83 measures the flow rate of test sample from the back pressure regulator 79 before being discharged through the waste container arm 167 and the waste container clamp 169 into the waste container 57. The waste container 57 is vented all the time through vent 171.

Sample Drop Counter and Flow Meter

Figure 6:
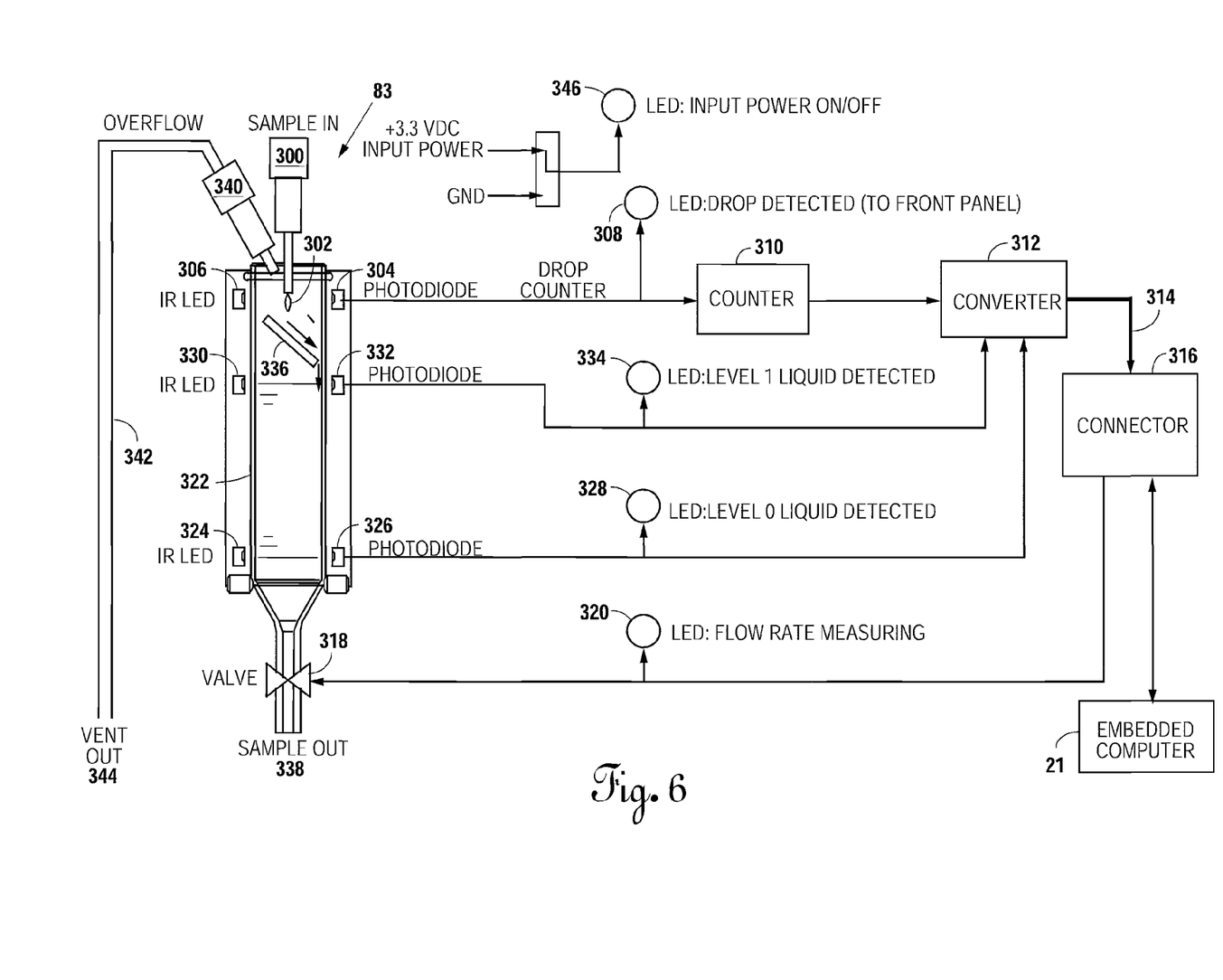
FIG. 6 is an elevated, partial sectional view of a drop counter and flow meter with a pictorial block diagram.

The sample drop counter and flow meter 83 as shown in FIG. 2 is shown in more detail in FIG. 6. A sample in 300 is from the back pressure regulator 79 shown in FIG. 2. Since the flow rate is very low, the sample in 300 will be in the form of drops 302. As the drops 302 are released, the drops will interrupt the light from the infrared LED 306 that is being received by the photodiode 304. When that occurs, LED 308 lights up indicating that a drop has been detected. Also, the signal from photodiode 304 that indicates a drop has been received is also fed to counter 310. Since the counter 310 is a straight binary counter, converter 312 changes the parallel signal to a serial signal. The serial signal connects over a four-wire bus 314 to connector 316. Connector 316 connects to embedded computer 21 previously shown in connection with FIG. 2.

At the beginning of a volumetric flow rate measurement, the valve 318 is closed by a signal from embedded computer 21 via connector 316. The signal also lights up LED 320 indicating a flow rate measurement is taking place. Thereafter, drops 302 of the test sample accumulates in the sample flow container 322. Once enough drops 302 of the test sample have accumulated in the sample flow container 322, level zero measured by infrared LED 324 and photodiode 326 will be reached. A level zero of fluid will interrupt light from the infrared LED 324 so that it is not received by a photodiode 326 which sends a signal through the converter 312 and connector 316 to the embedded computer 21. Simultaneously, the LED 328 is lit up indicating the level zero of sample liquid has been detected. This also starts the beginning of a timing cycle to determine the flow rate.

Thereafter, as drops 302 of the test liquid continue to accumulate inside of sample flow container 322, level one of the fluid will be detected when the infrared signal from the infrared LED 330 is interrupted so that it is no longer received by photodiode 332. This sends a signal through converter 312 and connector 316 to the embedded computer 21. Simultaneously, LED 334 will be lit indicating the sample liquid has reached level one.

By knowing the exact size of a sample flow container 322 between level zero and level one, the flow rate of the fuel under test can be accurately determined. In a prototype built by Applicant, there was a 9 mL volume between level zero and level one.

To keep the drops 302 from interfering with the signals from either (a) infrared LED 330 and photodiode 332 or (b) infrared LED 324 and photodiode 326, a deflector 336 is contained within sample flow container 332 below the forming of the drops 302, but above infrared LED 330 and photodiode 332. The deflector 336 directs the drops 302 to the inside wall of the sample flow container 322 so that the drops run down the inside wall thereof. In this manner, the drops 302 will not interfere with the infrared signals being picked up by either photodiode 326 or photodiode 332. The deflector 336 may be made from glass or any other material that is not corrosive when coming in contact with fuels or similar materials.

Once level one of the liquid under test has been detected by photodiode 332 and the signal sent through converter 312 and connector 316 to embedded computer 21, the embedded computer 21 can then send a signal back through connector 316 to open valve 318. The sample out 338 received from valve 318 goes to the waste container 57 shown in FIG. 2. To prevent pressure build up in the sample flow container 322, overflow connection 340 is provided to vent line 342 which connects to vent out 344. Vent out 344 is the same as the waste container vent shown in FIG. 2. To supply power to the components of sample flow meter 83, a positive 3.3 VDC is provided along with a ground connection from DC power distribution 99 as shown in FIG. 2A. When power is applied, LED 346 will light up indicating power has been received.

By use of the sample drop counter and flow meter 83 as just described in connection with FIG. 6, the flow rate of the test sample is accurately determined. Therefore, the flow rate of the fluid being tested is accurately checked. The sample drop counter and flow meter 83 is located after the heater tube test section, and therefore does not influence the results of the test.

What I claim is:
1. An apparatus for testing thermal oxidation stability of a test sample such as a hydrocarbon fuel comprising:
   a source of electric power;
   a heater tube connected to said source of electric power for flowing current to heat a center section of said heater tube to a predetermined temperature;
   a coolant flow circuit supplying coolant to each end of said heater tube to keep each end thereof near room temperature;
   an aeration circuit with an aeration pump for pumping air to aerate said test simple in a sample container;
   a test sample flow circuit for flowing said test sample around said center section to heat said test sample to said predetermined temperature, said test sample flow circuit including:
      a sample drive pump pumping said test sample from said sample container around said center section of said heater tube;
      a differential pressure filter in said test sample flow circuit after said heater tube to filter out any solids that may have formed in said test sample when heated to said predetermined temperature due to oxidation of said test sample;
      a differential pressure sensor for measuring differential pressure across said differential pressure filter;
      a back pressure regulator for maintaining said test sample being pumped by said sample drive pump at a test pressure high enough to keep said test sample in liquid phase when heated to said predetermined temperature;

a waste container for collecting said test sample after said test;

a sample flow meter connected to said test sample flow circuit for accurately measuring said test sample flowing there through.

2. The apparatus for testing thermal oxidation stability of said test sample as recited in claim 1 wherein said sample flow meter includes measuring fill time for said test sample to fill a flow rate measuring container from a first level to a second level.

3. The apparatus for testing thermal oxidation stability of said test sample as recited in claim 2 wherein said flow meter further comprises a given volume in said flow rate measuring container between said first level and said second level, a computer for calculating a flow rate by using said given volume and said fill time.

4. The apparatus for testing thermal oxidation stability of a test sample as recited in claim 3 wherein said flow meter includes a drop counter to measure drip time for said test sample, said drip time being used to calculate said flow rate in said computer.

5. The apparatus for testing thermal oxidation stability of said test sample as recited in claim 4 wherein said drop counter counts drops of said test sample received with a photo detector.

6. The apparatus for testing thermal oxidation stability of said test sample as recited in claim 5 wherein said flow meter has photo detectors for determining when said test sample in said flow rate measuring container reaches said first level and said second level.

7. The apparatus for testing thermal oxidation stability of said test sample as recited in claim 4 wherein the said drop counter and flow meter further comprises a deflector for directing said drops against inside walls of said flow rate measuring container.

8. The apparatus for testing thermal oxidation stability of said test sample as recited in claim 4 wherein said drop counter and flow meter has a vent for said flow rate measuring container to allow air to escape or enter said flow rate measuring container and a valve to drain said test sample from said flow rate measuring container.

9. The apparatus for testing thermal oxidation stability of said test sample as recited in claim 7 wherein said drop counter and flow meter has visual indicators when said test sample reaches said first level and said second level.

10. A method of testing a test sample in liquid form for thermal oxidation stability comprising the following steps:

aerating said test sample in a sample container with dry air to saturate said test sample with oxygen;

heating a center section of a heater tube to a predetermined temperature by flowing current there through;

cooling each end of said heater tube by flowing coolant from a coolant flow circuit to said each end;

pumping said test sample at a low flow rate around said center section of said heater tube so that a temperature of said test sample is raised to approximately said predetermined temperature;

test filtering with a differential pressure filter said test sample to collect solids formed in said test sample when heated to said predetermined temperature;

maintaining an elevated pressure on said test sample during said pumping step sufficient to keep said test sample from evaporating;

discharging said test sample through a drop counter and flow meter to a waste container.

11. The method of testing the test sample in liquid form for thermal oxidation stability as recited in claim 10 wherein said flow meter has a flow rate measuring container with a given volume between level zero and level one, photo detectors in said flow rate measuring container to detect when said test sample reaches level zero and thereafter level one.

12. The method of testing the test sample in liquid form for thermal oxidation stability as recited in claim 11 includes a further step of calculating flow rate by using said given volume and fill time for said test sample to accumulate from said level zero to said level one.

13. The method of testing the test sample in liquid form for thermal oxidation stability as recited in claim 11 includes an initial step of closing a valve from said flow rate measuring container and after said test sample reaches said level one, opening said valve.

14. The method of testing the test sample in liquid form for thermal oxidation stability as recited in claim 11 wherein said photo detectors are infrared LEDs and corresponding photodiodes.

15. The method of testing the test sample in liquid form for thermal oxidation stability as recited in claim 10 includes an additional step of counting drops and measuring drip time of said test sample entering said flow rate measuring container and using drip time of a predetermined number of drops counted to provide an automated drip rate method for a flow rate check.

16. The method of testing the test sample in liquid form for thermal oxidation stability as recited in claim 15 includes deflecting said drops to an inside wall of said flow rate measuring container before said second level.

17. The method of testing the test sample in liquid form for thermal oxidation stability as recited in claim 10 includes venting said flow rate measuring container for air and/or test sample overflow.

* * * * *